United States Patent [19]

Lindgren et al.

[11] Patent Number: 5,395,396
[45] Date of Patent: Mar. 7, 1995

[54] METHOD AND APPARATUS FOR STIMULATING A HEART

[75] Inventors: Anders Lindgren, Taeby; Per Franberg, Stockholm, both of Sweden

[73] Assignee: Siemens Elema AB, Solna, Sweden

[21] Appl. No.: 118,214

[22] Filed: Sep. 9, 1993

[30] Foreign Application Priority Data

Sep. 30, 1992 [SE] Sweden .............................. 9202826

[51] Int. Cl.[6] .............................................. A61N 1/368
[52] U.S. Cl. ............................................ 607/9; 607/14
[58] Field of Search .................................. 607/9, 14, 25

[56] References Cited

U.S. PATENT DOCUMENTS

| | | | |
|---|---|---|---|
| 4,539,991 | 9/1985 | Boute et al. | 607/9 |
| 4,890,617 | 1/1990 | Markowitz et al. | |
| 4,974,589 | 12/1990 | Sholder | 607/9 |
| 5,103,820 | 4/1992 | Markowitz . | |
| 5,123,412 | 6/1992 | Betzold . | |
| 5,129,393 | 7/1992 | Brumwell . | |

FOREIGN PATENT DOCUMENTS 0308535  9/1987  European Pat. Off. .

Primary Examiner—William E. Kamm
Assistant Examiner—Kennedy J. Schaetzle
Attorney, Agent, or Firm—Hill, Steadman & Simpson

[57] ABSTRACT

A heart stimulator is disclosed which is capable of sensing and stimulating both the atrium and the ventricle in a heart such that a ventricular stimulation pulse is emitted, either after expiration of an atrioventricular interval following a stimulated or spontaneous atrial event, or after expiration of a minimum synchronous interval following a stimulated or spontaneous ventricular event, depending on which of the two intervals expires last. After each ventricular event, an atrial refractory period is imposed during which atrial detections are interpreted as noise. Operation of the heart stimulator when the atrium's spontaneous rate is faster than a stimulation rate corresponding to the minimum synchronous interval is improved by measuring the interval between atrial events. If a detection during the atrium's refractory period occurs at a time corresponding to the latest interval timed, the detection is interpreted as an approved atrial event, and a ventricular stimulation pulse is emitted after expiration of the minimum synchronous interval.

18 Claims, 4 Drawing Sheets

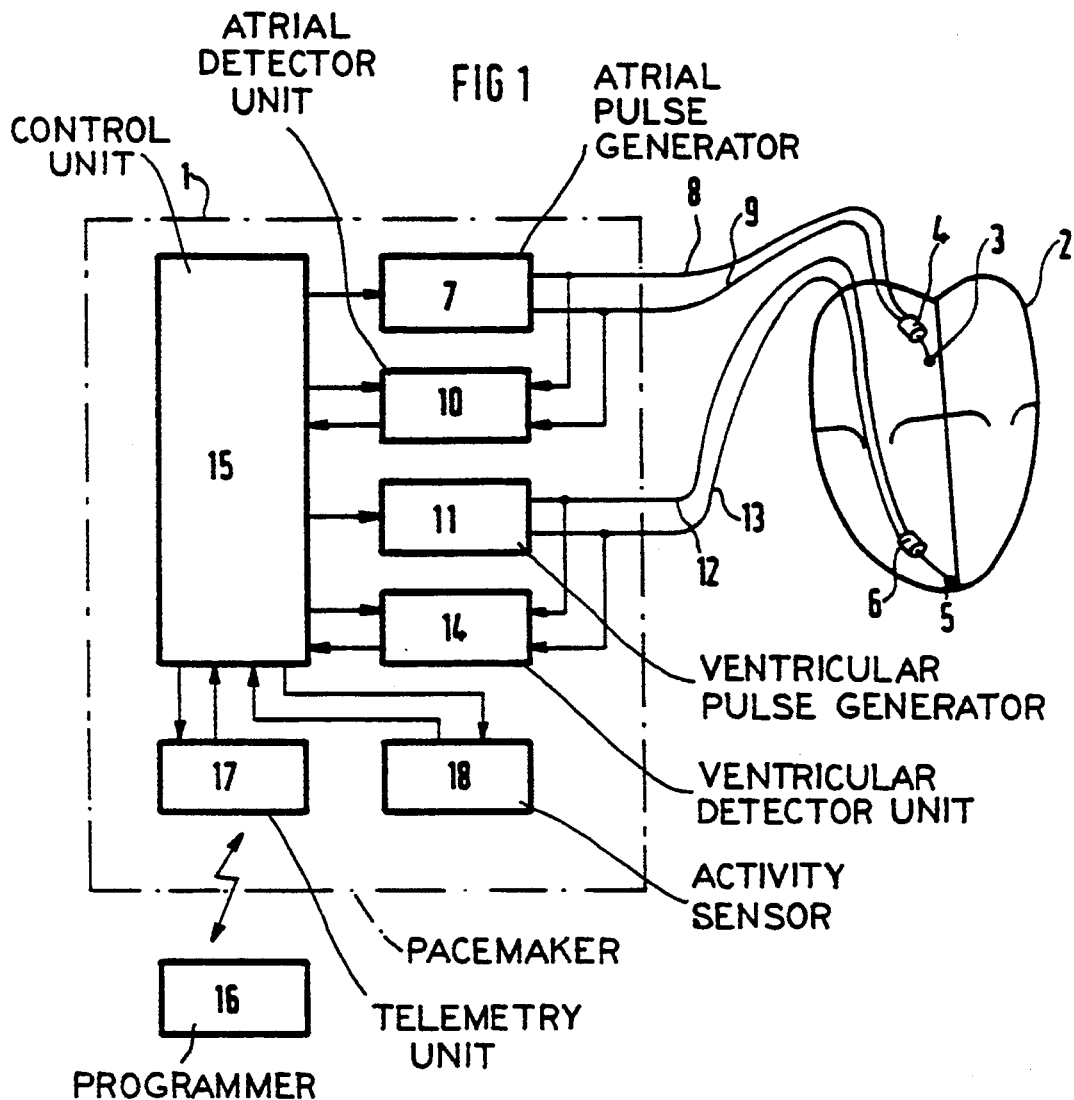

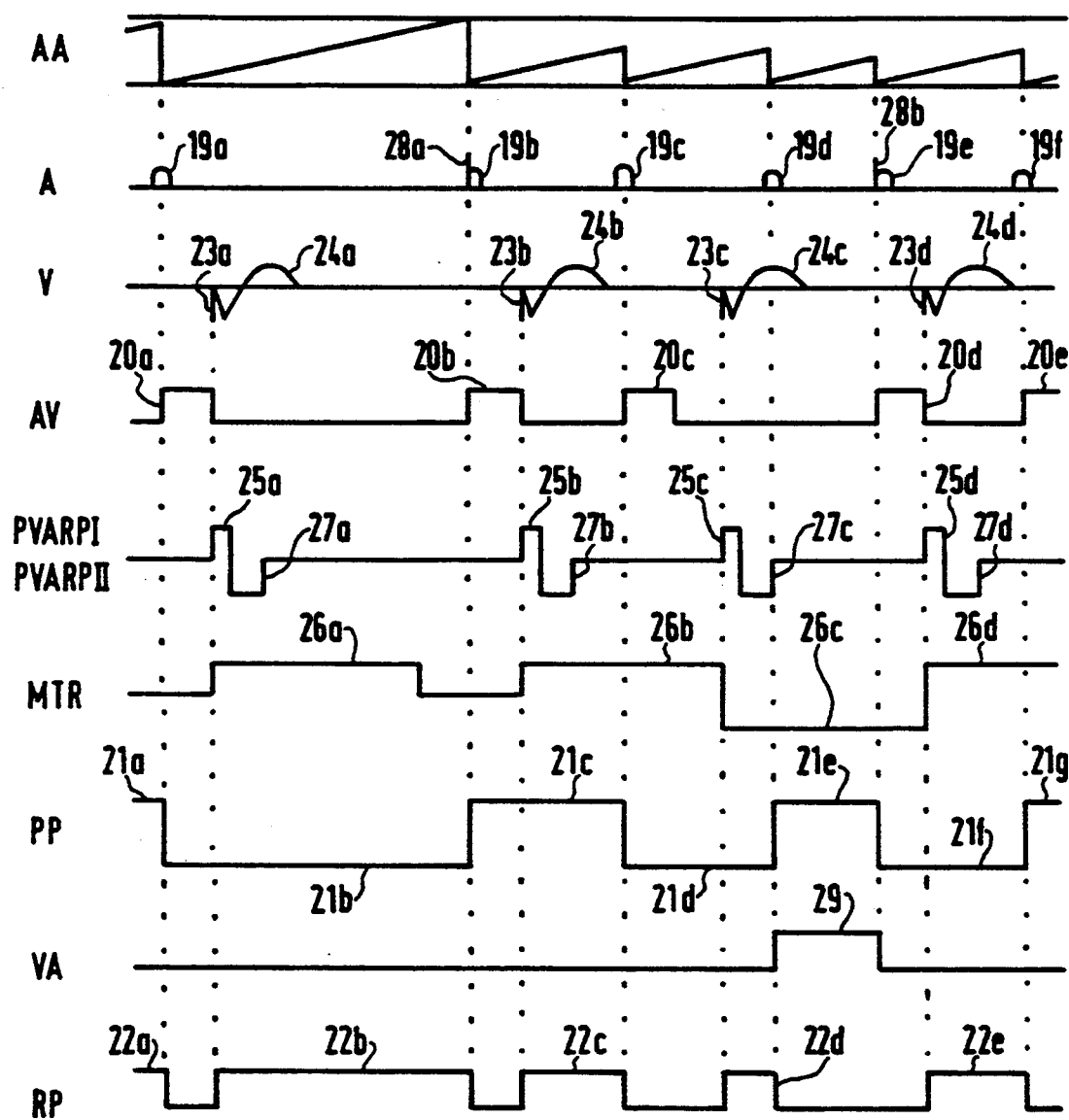

METHOD AND APPARATUS FOR STIMULATING A HEART

BACKGROUND OF THE INVENTION

Related Applications

This application is related to co-pending application Ser. No. 08/118,215 ("METHOD AND APPARATUS FOR STIMULATING A HEART," A. Lindgren) filed simultaneously herewith and assigned to the same assignee (Siemens AG) as the present application.

Field of the Invention

The present invention relates to methods and devices for stimulating (pacing) a heart, and more particularly to dual chamber pacing devices and methods.

Description of the Prior Art

Pacemakers are known which include an atrial pulse generator for stimulating atrial events, an atrial detector unit for detecting atrial events, a ventricular pulse generator for stimulating ventricular events, a ventricular detector unit for detecting ventricular events and a control unit for controlling the pulse generators on the basis of events detected by the detectors. The atrial stimulation pulses are emitted at a programmable basic interval, with a next atrial stimulation pulse being inhibited if a spontaneous atrial event is detected. Ventricular stimulation pulses being emitted either after expiration of a first atrioventricular interval, following an inhibited stimulation pulse or a stimulated or spontaneous atrial event, or after expiration of a minimum synchronous interval following a stimulated or spontaneous ventricular event, depending on which of the two intervals elapses last. The control unit interprets atrial detections as noise during a preset refractory period following emission of a ventricular stimulation pulse.

A heart stimulator is described in U.S. Pat. No. 4,890,617 which is designed to sense and stimulate both the atrium and ventricle in a heart. The heart stimulator operates synchronously after spontaneous atrial events by imposing an atrioventricular interval, i.e., an A-V interval, after every detected atrial event. A ventricular stimulation pulse is emitted after the expiration of the A-V interval if no ventricular event was detected in the A-V interval. If the atrium's spontaneous pulse rate slows until the interval between two atrial spontaneous events becomes too long, the heart stimulator takes over and stimulates the atrium at a basic interval, i.e., the A-A interval. After emission of every atrial stimulation pulse, an A-V interval is imposed after whose expiration a ventricular stimulation pulse is emitted. If the spontaneous pulse rate instead increases so that the interval between spontaneous events in the atrium becomes too short, emission of ventricular stimulation pulses is limited by a minimum synchronous interval corresponding to a fastest permissible synchronous stimulation rate. In the event of extensive atrial activity, the heart stimulator will wait for the minimum synchronous interval to expire before emitting a ventricular stimulation pulse. Since the interval elapsing between spontaneous atrial events is shorter than the interval between emitted ventricular stimulation pulses, the interval elapsing between an atrial event and the next ventricular stimulation pulse will increase in each heart cycle. This continues until an atrial event occurs during the atrial refractory period after every emitted ventricular stimulation pulse. The heart stimulator does not interpret atrial events occurring during the refractory period as "approved" atrial events, so the next ventricular stimulation pulse is synchronized with the next atrial event, spontaneous or stimulated. This is known as "Wenckebach blocking". Accordingly, emission of the next ventricular stimulation pulse can occur no later than after expiration of the basic interval, A-A, from the latest approved atrial event detected plus the following A-V interval.

Since the aforementioned known heart stimulator is rate-responsive, i.e., it is capable of stimulating a patient according to the patient's level of physical activity, the basic interval depends on the signal measured by an activity sensor. Therefore, prolongation of the interval between two ventricular stimulation pulses in Wenckebach blocking could even be limited by a basic interval shortened by a high level of physical activity by the patient.

Operation of this known heart stimulator When the spontaneous atrial pulse rate is faster than the fastest permissible synchronous ventricular stimulation rate causes certain problems. The next ventricular stimulation pulse is displaced every time Wenckebach blocking occurs. This results in irregular stimulation of the ventricle during the period in which the atrial pulse rate is faster than the fastest permissible synchronous rate. This could be uncomfortable for the pacemaker patient.

Moreover, an increased interval between atrial and ventricular events gives the atrium the time to biologically repolarize before the ventricular stimulation pulse is emitted. As a result, the ventricular stimulation pulse could be conducted to the atrium and stimulate an atrial event. Conduction time is normally longer than the atrial refractory period, so the heart stimulator would then interpret this event as an approved spontaneous atrial event. The heart stimulator could then become unable to exit a loop in which conducted atrial events initiate ventricular stimulation pulses. This is referred to as pacemaker mediated tachycardia, PMT.

Another risk with an excessively long interval between an atrial event and the next ventricular stimulation pulse is that the next spontaneous atrial event could occur at the same time as, or immediately after, the ventricular stimulation pulse. The ventricle in this situation is in a contracted state, and pressure in the ventricle keeps the heart valves between the atrium and the ventricle closed. When the atrium contracts, blood in the atrium will be pumped in the wrong direction, i.e., out of the atrium into the vascular system. This phenomenon is known as the pacemaker syndrome. In addition to being unpleasant to the patient, the process impairs cardiac function. Reflux of blood is impaired during the next heart cycle, the atrium's pumping effect is degraded, and the autonomic nervous system could interpret the retrograde pressure wave as excessively high blood pressure. The body may then react to generate drop in blood pressure leading to fatigue, reduced exercise capacity, dizziness and nausea in the patient. At worst, the drop in blood pressure could be severe enough to cause the patient to faint.

SUMMARY OF THE INVENTION

It is an object of the present invention to provide a heart stimulator and a heart stimulating method which achieves more uniform stimulation of the ventricle when atrial activity is high.

It is also an object of the invention to achieve a heart stimulator and method which prevent the development of PMT and pacemaker syndrome.

The above objects are achieved in a heart stimulator constructed and operating according to the invention, having respective atrial and ventricular stimulators (pulse generators) and event detectors, and a control unit, wherein the control unit measures the interval between successive atrial events which are spontaneous atrial events, and if the interval between a number of consecutively timed atrial events of any type is less than the minimum synchronous interval, an atrial detection in the refractory period occurring at a time corresponding to the latest interval timed is interpreted as an "approved" atrial event, and the ventricular pulse generator emits the next ventricular stimulation pulse after the minimum synchronous interval expires until the timed interval exceeds the minimum synchronous interval for a preset number of consecutive atrial events.

As a rule, the interval between spontaneous atrial events is very regular when the level of atrial activity is high, so this time can be used as a check as to whether detections during the atrial refractory period are caused by an atrial event or a ventricular event. If the atrial detection occurs after the latest atrial event at an interval which is as long as the latest timed interval between two atrial events, the atrial detection is in all probability a spontaneous atrial event. Therefore, as long as atrial activity is faster than the atrium's fastest atrial synchronous stimulation rate, stimulation of the ventricle at the fastest synchronous stimulation rate results in the most uniform stimulation of the ventricle. The irregular stimulation of the ventricle which arises in the current state of the art does therefore not occur with the present invention.

In this context, the control unit preferably controls the ventricular pulse generator, when the interval between spontaneous atrial events is shorter than a threshold interval, so that the ventricular pulse generator increases the interval between emitted ventricular stimulation pulses for a preset number of stimulation cycles until a preset safety interval is achieved, whereupon the ventricular pulse generator emits ventricular stimulation pulses at the preset safety interval. The ventricular pulse generator continues to emit ventricular stimulation pulses at the preset safety interval as long as the interval between spontaneous atrial events is shorter than the threshold interval.

Atrial fibrillation or flutter are usually involved when the level of atrial activity is excessively fast, i.e., non-physiological activity. Stimulation of the ventricle at some rate other than the fastest synchronous rate is then better for the patient. However, the transition from one rate to another should be gentle, not abrupt, and therefore occur in stages.

In a further embodiment of the heart stimulator and method according to the invention, the control unit imposes an extra atrial stimulation pulse at a second preset atrioventricular interval before the next ventricular stimulation pulse if the interval between the latest atrial event sensed and the next ventricular stimulation pulse exceeds a preset threshold value. This limits the interval between an atrial event and the next ventricular stimulation pulse, minimizing the risk of PMT or pacemaker syndrome, since the extra atrial stimulation pulse prevents a spontaneous atrial event from occurring before the atrium has repolarized. The extra atrial stimulation pulse also makes an additional contribution to the filling of the ventricle with blood.

In this context, the control unit preferably inhibits the extra atrial stimulation pulse when an atrial event is detected after the latest atrial event detected and before the minimum synchronous interval has elapsed. There is no reason for emission of an extra atrial stimulation pulse if the interval between a spontaneous atrial event and the next ventricular stimulation pulse does not exceed the threshold value.

The threshold value is preferably selected to consist of an interval corresponding to the atrium's biological refractory period plus the second atrioventricular interval, preferably between 300 and 500 ms.

In a further embodiment of the heart stimulator and method in accordance with the invention, the control unit measures the time elapsing from the latest stimulated or spontaneous ventricular event to the next sensed atrial event and compares this measured time to the minimum synchronous interval minus the threshold value to ascertain whether the interval between the latest atrial event sensed and the next ventricular stimulation pulse exceeds the threshold value. If the timed interval is less than the minimum synchronous interval minus the threshold value, the control unit determines whether the interval exceeds the threshold value.

Since the minimum synchronous interval and threshold value are known, programmable parameters, the difference between them is easily determined. When the threshold value corresponds to the interval between one atrial event and the next ventricular stimulation, which cannot occur before the minimum synchronous interval expires, the interval will reliably exceed the threshold value when the time elapsing between the latest ventricular event and the next atrial event sensed is less than the difference between the minimum synchronous interval and the threshold value.

Preferably the control device, when the interval exceeds the threshold value, imposes a ventriculoatrial interval after whose expiration the atrial pulse generator emits the extra atrial stimulation pulse, the ventricular pulse generator then emitting the ventricular stimulation pulse after the second atrioventricular interval expires.

The ventriculoatrial interval designates the time during which the atrium is sensed following spontaneous stimulation pulses, which can inhibit emission of the extra atrial stimulation pulse.

In this context, preferably the control unit sets the duration of the ventriculoatrial interval to consist of the minimum synchronous interval minus the sum of the time elapsing from the latest ventricular event to the next atrial event sensed and the duration of the second atrioventricular interval. This ensures that the ventricular stimulation pulse is emitted after expiration of the minimum synchronous interval when atrial activity is excessively fast.

DESCRIPTION OF THE DRAWINGS

FIG. 1 is a schematic block diagram of a heart stimulator constructed in accordance with the principles of the present invention and operating according to the inventive method.

FIG. 3 shows, in a time diagram, a number of heart cycles illustrating the function of the heart stimulator of FIG. 1 over a course of events.

DESCRIPTION OF THE PREFERRED EMBODIMENTS

Figure 2A:
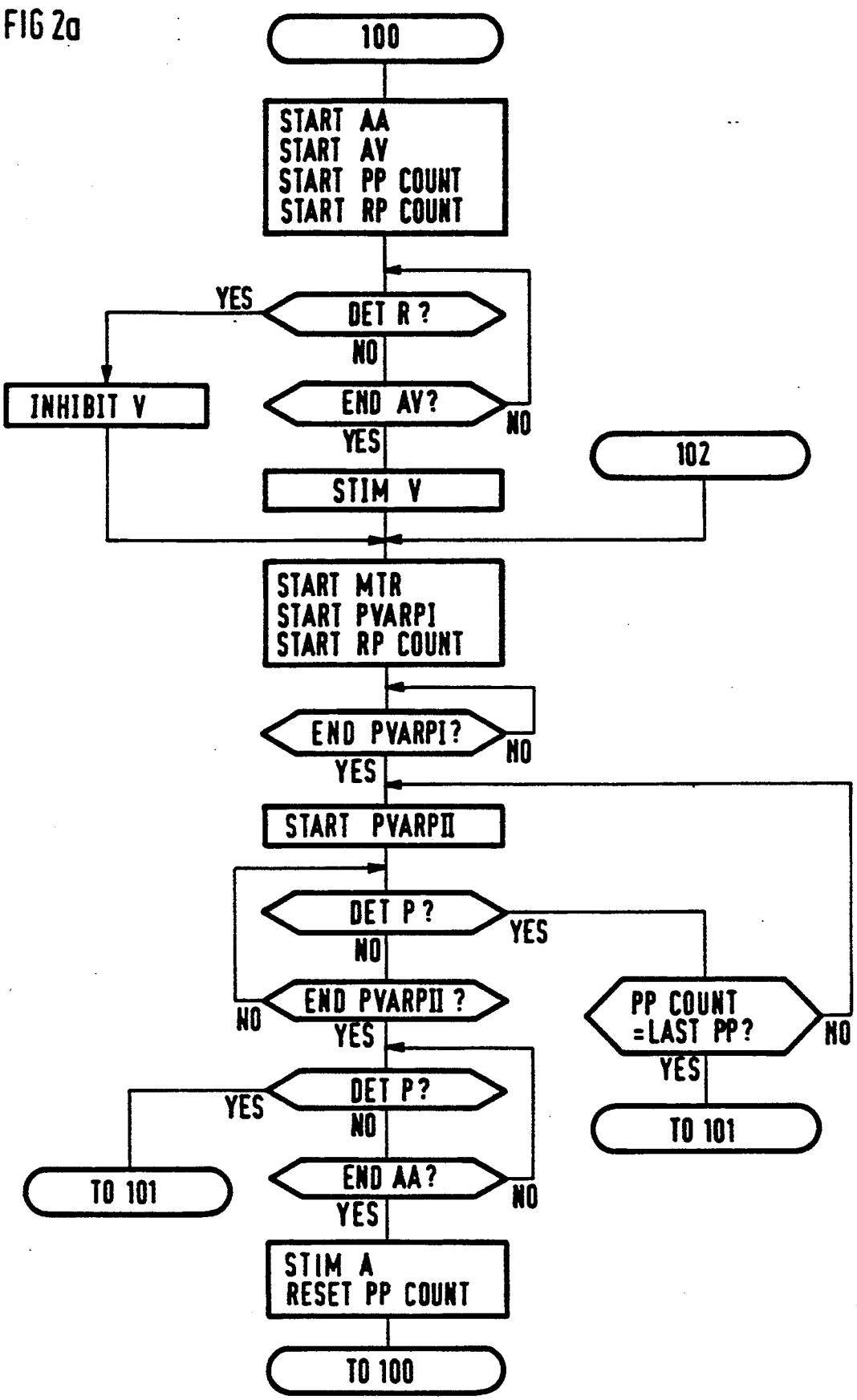
FIGS. 2a and 2b in combination show a flowchart for functions which can be performed with the heart stimulator of FIG. 1.

The heart stimulator of FIG. 1 is in the form of a bipolar dual chamber pacemaker 1. The pacemaker 1 is connected to the atrium in a heart 2 via a first tip electrode 3 and a first ring electrode 4 and to the ventricle of the heart 2 via a second tip electrode 5 and a second ring electrode 6. An atrial pulse generator 7 in the pacemaker 1 is respectively connected by a first electrode conductor 8 and a second electrode conductor 9 to the first ring electrode 4 and the first tip electrode 3 respectively so as to deliver atrial stimulation pulses. An atrial detector unit 10 for sensing atrial events is connected in parallel with the atrial pulse generator 7.

In a corresponding manner, a ventricular pulse generator 11 is respectively connected to the second ring electrode 6 and the second tip electrode 5 by a third electrode conductor 12 and a fourth electrode conductor 13, for emitting ventricular stimulation pulses. A ventricular detector unit 14 for sensing ventricular events is connected in parallel with the ventricular pulse generator 11.

The pulse generators 7 and 11 are controlled by a control unit 15 which controls the emission of stimulation pulses with respect to timing, amplitude and duration. The control unit 15 also controls the detector units 10 and 14 and receives information about sensed events therefrom.

A physician, using an external programming unit 16, can check and change program parameters in the control unit 15. Communication between the control unit 15 and the programming unit 16 is established via a telemetry unit 17, connected to the control unit 15, which transmits/receives information to/from the programming unit 16.

The pacemaker 1 contains an activity sensor 18 for sensing the pacemaker patient's physical activity, enabling the control unit 15 to adapt the stimulation rate to the patient's level of physical activity.

The pacemaker 1 operates with an inhibitory function. This means that no stimulation pulses are supplied as long as the heart 2 spontaneously functions at an adequate rate. If, e.g., only the atrium functions spontaneously at an adequate rate, the ventricular pulse generator emits a ventricular stimulation pulse after expiration of an atrioventricular interval, the A-V interval, which starts when an atrial event is sensed. To keep the ventricle from being stimulated at an excessively fast rate when the atrium's spontaneous pulse rate is too fast, emission of ventricular stimulation pulses is limited by a maximum synchronous stimulation rate, MTR. However, "MTR" will henceforth designate the minimum synchronous interval corresponding to the maximum synchronous rate. MTR is programmable and set by a physician.

Figure 2B:
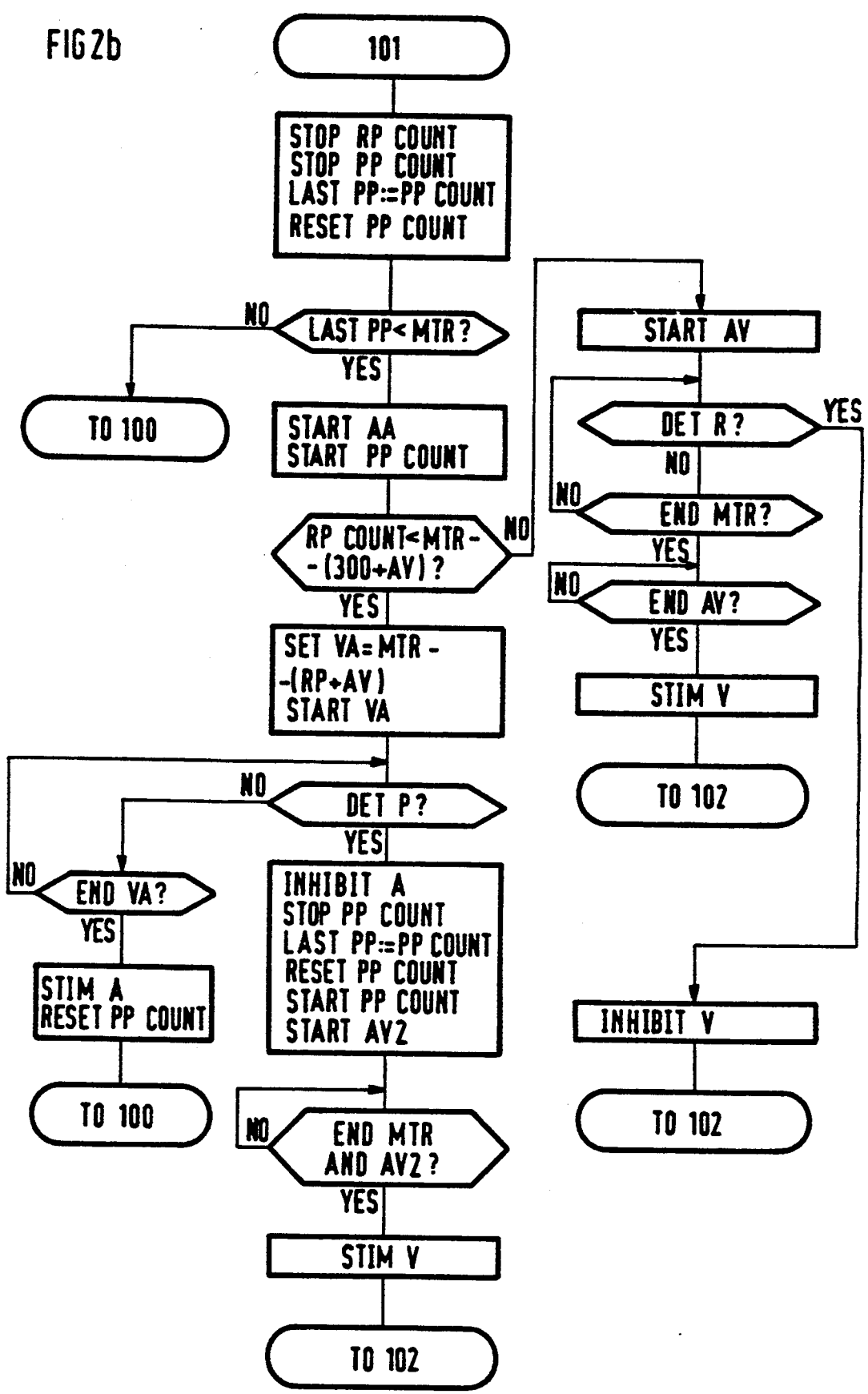

A flowchart is shown in FIGS. 2a and 2b which schematically describes functions the pacemaker 1 can perform to optimize the pacemaker's operation when the atrium's spontaneous pulse rate is faster than the MTR. In the flow chart, A designates atrial events in general, P spontaneous atrial events, V ventricular events in general and R spontaneous ventricular events. AA designates a basic interval for the atrium at which the pacemaker 1 stimulates the atrium if the atrium's spontaneous pulse rate slows too much. The basic interval AA can be controlled by the patient's level of physical activity when the activity sensor 18 is activated by the control unit 15. RP designates the interval elapsing between a ventricular event (spontaneous or stimulated) and the next atrial event. Other designations will be explained as introduced.

The first function block in FIG. 2a, following block 100, designates the sequence after a spontaneous or stimulated atrial event. The A-A interval and an A-V interval start, timing of a P-P interval starts and timing of an R-P interval is zeroed. The ventricle is sensed in the next block (DET R?). If a ventricular event is detected (exit YES), emission of the ventricular stimulation pulse is inhibited (INHIBIT V), and the pacemaker 1 continues operation. If no ventricular event is sensed (exit NO in block DET R?), expiration of the A-V interval (exit YES block END AV?) is awaited before a ventricular stimulation pulse is emitted (STIM V). After a ventricular event (stimulated or spontaneous), an MTR interval, timing of the R-P interval and an absolute atrial refractory period PVARPI start. The atrial detector unit 10 is inactive during the refractory period PVARPI, since the ventricular stimulation pulse causes noise making it very difficult to discriminate signals corresponding to an atrial event. After the refractory period PVARPI expires, a relative atrial refractory period PVARPII starts (START PVARPII). The atrial detector unit 10 is activated during the relative atrial refractory period PVARPII in order to sense the atrium. Detections during the relative atrial refractory period PVARPII are normally interpreted as noise from the ventricular event and only cause PVARPI I to restart. According to the present invention, however, a check is first made to determine whether the interval between the latest atrial event and the detection during the period PVARPII corresponds to the latest timed interval between two atrial events (PP COUNT-=LAST PP?).

The relative atrial refractory period PVARPII restarts if detection in the PVARPII does not correspond to the latest timed interval between two atrial events (exit NO). If detection in the period PVARPII corresponds to the latest time measured between two atrial events (exit YES), operation continues with block 101 in FIG. 2b, as described in detail below.

If no detections are sensed during the period PVARPII, operation continues by sensing the atrium during the rest of the A-A interval. If an atrial event is sensed during this period, operation continues according to block 101 in FIG. 2b. Otherwise, expiration of the A-A interval is awaited (exit YES block END AA?), whereupon the atrium is stimulated, and timing of the P-P interval is zeroed, since only spontaneous atrial events can terminate the timing of a natural P-P interval. Operation then continues at block 100 as described above.

In FIG. 2b the flowchart describes operation when an atrial detection occurs in the relative atrial refractory period PVARPII and is accepted as an atrial event or when a detection occurs between expiration of the period PVARPII and expiration of the A-A interval. Timing of the RP interval and the P-P interval is then stopped. Since an approved atrial event is present, the latest timed interval is assigned the same duration as the current timed interval (LAST PP := PP COUNT), and timing of the current P-P interval is zeroed. The latest P-P interval is then compared to the MTR interval (LAST PP < MTR?). If the latest P-P interval is not less than the MTR interval (exit NO), operation continues according to block 100 in FIG. 2a. If the latest P-P interval is less than the MTR interval (exit YES), a new A-A interval starts, followed by timing of the present P-P interval, whereupon the timed R-P interval is compared with the MTR interval minus 300 plus the A-V interval (RP COUNT<MTR−(300+AV?)). If the timed R-P interval is shorter, this means that the interval between the detected atrial event and expiration of the MTR interval is so long that an extra atrial stimulation pulse must be emitted before the ventricular stimulation pulse is emitted. In this instance, a V-A interval is set (SET VA=...) at a duration corresponding to the MTR minus the timed R-P interval plus the A-V interval. The V-A interval then starts (START VA). The atrium is sensed for spontaneous atrial events (DET P?) while the V-A interval is elapsing. If no atrial event is sensed before the V-A interval expires (exit YES block END VA?), the atrium is stimulated, and timing of the present P-P interval is zeroed before operation continues at block 100 according to FIG. 2a.

If an atrial event is sensed during the V-A interval (exit YES block DET P?), emission of the extra stimulation pulse is inhibited at the same time as timing of the current P-P interval stops, and the latest P-P interval is assigned the same value as the timed duration of the present P-P interval. Timing of the P-P interval is then zeroed and restarted. At the same time, a shortened A-V interval starts (start AVII). The purpose of this shortened A-V interval is to permit emission of the ventricular stimulation pulse as close as possible to expiration of the MTR interval. According to the function diagram, expiration of the MTR and AVII intervals is awaited (END MTR AND AVII). A ventricular stimulation pulse is then emitted when both intervals have expired, and operation continues according to block 102 in FIG. 2a.

If the timed R-P interval had not been shorter than the MTR interval minus 300 plus the A-V interval (exit NO block RP COUNT<MTR−(300+AV?)), an A-V interval would have been started during which the ventricle would be sensed for spontaneous ventricular events (DET R?). If a ventricular event is sensed (exit YES), the ventricular stimulation pulse is inhibited (INHIBIT V), and operation continues according to block 102 in FIG. 2a. If no detection is sensed in the MTR interval (exit YES block END MTR?), expiration of the A-V interval is awaited (END AV?), whereupon a ventricular stimulation pulse is emitted (STIM V), and operation continues according to block 102 in FIG. 2a.

FIG. 3 illustrates, in a time diagram, the operation described in conjunction with the flowchart in FIGS. 2a and 2b. FIG. 3 shows the following parameters in this order: the A-A interval, events in the atrium (A), events in the ventricle (V), the A-V interval, the PVARPI period, the PVARPII period, the MTR interval, the P-P interval, the V-A interval and the R-P interval.

In FIG. 3, the diagram begins with a spontaneous atrial event 19a. The atrial event 19a zeroes and restarts timing of the A-A interval, starts an A-V interval 20a, stops timing of the present P-P interval 21a and the R-P interval 22a and starts timing of a new P-P interval 21b. When the A-V interval 20a expires without any other events occurring, a ventricular stimulation pulse 23a is emitted which causes a stimulated ventricular event 24a. At the same time, a PVARPI period 25a, during which there is no sensing of atrial activity, an MTR interval 26a and timing of the next R-P interval 22b start. When the PVARPI period 25a expires, a PVARPII period 27a starts, during which the atrium is sensed and detections are compared with the latest timed P-P interval 21a to ascertain whether the detection is an approved atrial event or noise from the ventricular event. In this instance, no events occur in the PVARPII period 27a or in the rest of the A-A interval, and an atrial stimulation pulse 28a is therefore emitted when the A-A interval expires. The atrial stimulation pulse 28a stimulates an atrial event 19b. At the same time as the atrial stimulation pulse 28a is emitted, timing of the A-A interval, as well as the next A-V interval, restarts. In addition, timing of the P-P interval 21b is zeroed, timing of the next P-P interval 21c starts and timing of the R-P interval 22b is stopped and zeroed. Since the P-P interval 21b was stopped by an emitted atrial stimulation pulse 28a, it does not correspond to a natural P-P interval, and the PP interval 21a still serves as the latest P-P interval.

After the AVI interval 20b expires, a ventricular stimulation pulse 23b is emitted at the same time as a new PVARPI period 25b, a new MTR interval 26b and renewed timing of an R-P interval 22c start. The ventricular stimulation pulse 23b causes a ventricular event 24b. When the PVARPI period 25b expires, a PVARPII period 27b starts during which no events occur. Before the A-A interval expires, an atrial event 19c is now detected which causes the timing of a new A-A interval and an AVI interval 20c. At the same time, timing of the present PP interval 21c and the R-P interval 22c stops. The timing of a new P-P interval 21d starts, and the P-P interval 21c now serves as the latest P-P interval. Since the R-P interval 22c is longer than the difference between the MTR interval 26b and the threshold value, no extra atrial stimulation pulse needs to be emitted. The MTR interval 26b has not yet expired at the time the A-V interval 20c expires, and the control unit 15 then waits for the MTR interval 26b to expire before ordering emission of a new ventricular stimulation pulse 23c. A PVARPI interval 25c, a new MTR interval 26c and timing of an R-P interval 22d start.

After the PVARPI period 25c expires, a PVARPII period 27c starts during which an atrial detection 19d occurs. The time elapsing from the latest atrial event 19c to the atrial detection 19d during the PVARPII period 27c is compared with the time elapsing from the atrial event 19b to the atrial event 19c, i.e., the latest P-P interval 21c. In this instance, detection during the PVARPII period 27c corresponds to this interval, and the atrial detection during that period is interpreted as an approved atrial event 19d. Since the event 19d is an approved atrial event, timing of a new A-A interval and a new P-P interval 21e starts at the same time as the timed P-P interval 21d is made to serve as the latest P-P interval. Timing of the R-P interval 22d is also concluded. The timed R-P interval 22d is now so brief that stimulation of the ventricle at the end of the MTR period 26c could lead to retrograde conduction to the atrium. Therefore, the control unit 15 does not impose an A-V interval, but instead imposes a V-A interval 29, after whose expiration an extra atrial stimulation pulse 28b is emitted. The atrial stimulation pulse 28b causes a stimulated atrial event 19e. At the same time, timing of a new A-A interval and a new P-P interval 21f starts. An A-V interval 20e also starts and expires at the same time as the MTR interval 26c. A ventricular stimulation pulse 23d is therefore emitted and stimulates a ventricular event 24d. A PVARPI period 25d, a new MTR interval 26d and renewed timing of an R-P interval 22e start at the same time. After expiration of the PVARPI period 25d, a PVARPII period 27d starts during which no events occur. Before the end of the AV interval, a spontaneous atrial event 19f is sensed, and an A-V interval 20e starts at the same time as timing of a new P-P interval 21f stops and timing of a new P-P interval 21g starts. The time interval 21f now serves as the latest P-P interval. Timing of the R-P interval 22e also stops at the same time as the atrial event 19f. The diagram then continues in the corresponding manner until the interval between spontaneous atrial events again exceeds the MTR interval.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for electrically stimulating a heart comprising the steps of:
   (a) detecting spontaneous and stimulated cardiac events in each of the atrium and the ventricle of a heart;
   (b) delivering a series of atrial stimulation pulses to said atrium at a programmable basic interval;
   (c) inhibiting delivery of an atrial stimulation pulse if a spontaneous atrial event is detected during said basic interval;
   (d) delivering a ventricular stimulation pulse after expiration of an atrioventricular interval following each inhibited or stimulated atrial pulse or a spontaneous atrial event, or after expiration of a minimum synchronous interval following a stimulated or spontaneous ventricular event, dependent on which of said atrioventricular interval or said minimum synchronous interval elapses last;
   (e) setting a refractory period following each ventricular stimulation pulse during which detection of an atrial event is normally interpreted as noise rather than as an atrial event;
   (f) measuring and updating each interval between consecutive atrial events which are spontaneous atrial events;
   (g) monitoring the interval between consecutive atrial events of any type and, if said interval between successive atrial events of any type is less than said minimum synchronous interval, interpreting an atrial event, occurring at a time lapse after a latest atrial event which corresponds to a latest interval between spontaneous atrial events, as an atrial event;
   (h) delivering a next ventricular pulse after said minimum synchronous interval expires; and
   (i) repeating steps (f), (g) and (h) until said interval between consecutive atrial events of any type exceeds said minimum synchronous interval, and thereafter returning to step (b).

2. A method as claimed in claim 1 comprising the additional steps of:
   if said interval between spontaneous atrial events is shorter than a predetermined threshold interval, increasing an interval between ventricular stimulation pulses for a predetermined number of stimulation cycles until said ventricular pulse are emitted at a predetermined safety interval; and
   continuing to emit said ventricular stimulation pulses at said predetermined safety interval as long as said interval between spontaneous atrial events is shorter than said threshold interval.

3. A method as claimed in claim 1 comprising the additional step of:
   delivering an extra atrial stimulation pulse after a second, predetermined atrioventricular interval before the a next ventricular stimulation pulse if an interval between a latest detected atrial event and said next ventricular stimulation pulse exceeds a predetermined threshold value.

4. A method as claimed in claim 3 comprising the additional step of:
   inhibiting the delivery of said extra atrial stimulation pulse if an atrial event is detected after said latest atrial event is detected and before the expiration of said minimum synchronous interval.

5. A method as claimed in claim 3 comprising the additional step of:
   setting said predetermined threshold value to consist of an interval corresponding to a biological refractory period of said atrium plus said second predetermined atrioventricular interval.

6. A method as claimed in claim 3 comprising the additional step of:
   setting said predetermined threshold value to a value between 300 and 500 ms.

7. A method as claimed in claim 3 comprising the additional steps of:
   measuring a time elapsing from a latest stimulated or spontaneous ventricular event to a next detected atrial event, thereby obtaining a measured time;
   comparing said measuring time to said minimum synchronous interval minus said threshold value and determining whether the interval between said latest detected atrial event and said next ventricular stimulation pulse exceeds said threshold value; and
   if said measured time is less than said minimum synchronous interval minus said threshold value, determining whether said measured time exceeds said threshold value.

8. A method as claimed in claim 7 comprising the additional steps of:
   if said measured time exceeds said threshold value, imposing a ventriculoatrial interval and permitting delivery of a next atrial stimulation pulse only after expiration of said ventriculoatrial interval; and
   delivering a next ventricular stimulation pulse after expiration of said second, predetermined atrial ventricular interval.

9. A method as claimed in claim 8 comprising the additional step of:
   setting a duration of said ventriculoatrial interval to consist of said minimum synchronous interval minus the sum of a time elapsing from a latest detected ventricular event to a next detected atrial event and the duration of said second predetermined atrioventricular interval.

10. An apparatus for electrically stimulating a heart comprising the steps of:
    means for detecting spontaneous and stimulated cardiac events in each of the atrium and the ventricle of a heart;

means for delivering a series of atrial stimulation pulses to said atrium at a programmable basic interval;

a control unit including means for inhibiting delivery of an atrial stimulation pulse if a spontaneous atrial event is detected during said basic interval;

said control unit further including means for causing delivery of a ventricular stimulation pulse after expiration of an atrioventricular interval following each inhibited or stimulated atrial pulse or a spontaneous atrial event, or after expiration of a minimum synchronous interval following a stimulated or spontaneous ventricular event, dependent on which of said atrioventricular interval or said minimum synchronous interval elapses last;

said control unit further including means for setting a refractory period following each ventricular stimulation pulse during which detection of an atrial event is normally interpreted as noise rather than as an atrial event;

said control unit further including means for measuring and updating each interval between consecutive atrial events which are spontaneous atrial events;

said control unit including means for monitoring the interval for between consecutive atrial events of any type, and if said interval between successive atrial events of any type is less than said minimum synchronous interval, for interpreting an atrial event, occurring at a time lapse after a latest atrial event which corresponds to a latest interval between spontaneous atrial events, as an atrial event and for delivering a next ventricular pulse after said minimum synchronous interval expires, until said interval between consecutive atrial events of any type exceeds said minimum synchronous interval.

11. An apparatus as claimed in claim 10 wherein said control unit further includes:

means, if said interval between spontaneous atrial events is shorter than a predetermined threshold interval, for increasing an interval between ventricular stimulation pulses for a predetermined number of stimulation cycles until said ventricular pulse are emitted at a predetermined safety interval; and means for causing said ventricular stimulation pulses to be emitted at said predetermined safety interval as long as said interval between spontaneous atrial events is shorter than said threshold interval.

12. An apparatus as claimed in claim 10 wherein said control unit further includes:

means for causing delivery of an extra atrial stimulation pulse after a second, predetermined atrioventricular interval before the a next ventricular stimulation pulse if an interval between a latest detected atrial event and said next ventricular stimulation pulse exceeds a predetermined threshold value.

13. An apparatus as claimed in claim 12 wherein said control unit further includes:

means for inhibiting the delivery of said extra atrial stimulation pulse if an atrial event is detected after said latest atrial event is detected and before the expiration of said minimum synchronous interval.

14. An apparatus as claimed in claim 12 wherein said control unit further includes:

means for setting said predetermined threshold value to consist of an interval corresponding to a biological refractory period of said atrium plus said second predetermined atrioventricular interval.

15. An apparatus as claimed in claim 12 wherein said control unit further includes:

means for setting said predetermined threshold value to a value between 300 and 500 ms.

16. An apparatus as claimed in claim 12 wherein said control unit further includes:

means for measuring a time elapsing from a latest stimulated or spontaneous ventricular event to a next detected atrial event, thereby obtaining a measured time;

means for comparing said measuring time to said minimum synchronous interval minus said threshold value and for determining whether the interval between said latest detected atrial event and said next ventricular stimulation pulse exceeds said threshold value; and means, if said measured time is less than said minimum synchronous interval minus said threshold value, for determining whether said measured time exceeds said threshold value.

17. An apparatus as claimed in claim 16 wherein said control unit further includes:

means, if said measured time exceeds said threshold value, for imposing a ventriculoatrial interval and for permitting delivery of a next atrial stimulation pulse only after expiration of said ventriculoatrial interval; and means for causing delivery of a next ventricular stimulation pulse after expiration of said second, predetermined atrial ventricular interval.

18. An apparatus as claimed in claim 17 wherein said control unit further includes:

means for setting a duration of said ventriculoatrial interval to consist of said minimum synchronous interval minus the sum of a time elapsing from a latest detected ventricular event to a next detected atrial event and the duration of said second predetermined atrioventricular interval.

* * * * *